United States Patent [19]

Wolff et al.

[11] 4,128,438
[45] Dec. 5, 1978

[54] GRANULATE FORM ORGANOSILANE PREPARATION

[75] Inventors: Siegfried Wolff, Bornheim-Merten; Lothar Rothbuhr, Hurth-Hermulheim, both of Germany

[73] Assignee: Deutsche Gold- und Silber-Scheideanstalt vormals Roessler, Frankfurt, Germany

[21] Appl. No.: 873,967

[22] Filed: Jan. 31, 1978

[30] Foreign Application Priority Data

Oct. 21, 1977 [DE] Fed. Rep. of Germany ....... 2747277

[51] Int. Cl.$^2$ .................. C08J 3/12; C08K 3/04; C08K 3/34; C09C 1/58
[52] U.S. Cl. .................. 106/307; 106/287.13; 106/287.14; 106/287.16; 252/182; 260/42.15; 260/42.32; 264/117
[58] Field of Search .................. 106/308 Q, 307; 264/117

[56] References Cited

U.S. PATENT DOCUMENTS

| 3,873,489 | 3/1975 | Thurn et al. | 106/308 Q X |
| 3,923,680 | 12/1975 | Roeder et al. | 264/117 X |
| 4,005,170 | 1/1977 | Harris | 264/117 X |

Primary Examiner—Helen McCarthy
Attorney, Agent, or Firm—Cushman, Darby & Cushman

[57] ABSTRACT

A granulate organosilane preparation is made consisting essentially of (a) 30 to 60 weight percent of at least one organosilane of the formula

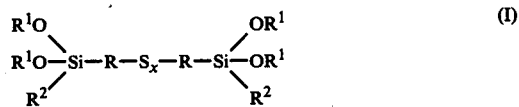

where $R^1$ is an alkyl group with 1 to 3 carbon atoms, $R^2$ is an alkyl or alkoxy group with 1 to 3 carbon atoms, R is an alkylene group with 1 to 5 carbon atoms and x has a value from 2.0 to 6.0, and (b) 70 to 40 weight percent of carbon black.

11 Claims, No Drawings

GRANULATE FORM ORGANOSILANE PREPARATION

BACKGROUND OF THE INVENTION

The invention is directed to non-dusting, pourable granulate form preparations made from organosilanes liquid at room temperature and specific types of carbon black. The silane preparations are characterized particularly by surprisingly good storage stability, by resistance to hydrolysis of the silane component and by easy workability into rubber mixtures. A series of organosilicon compounds as is known is recommended and used in rubber technology. Especially known are sulfur containing alkoxysilanes which are predominantly suited as adhesive agents and reinforcers for vulcanizates of silica filler containing rubber mixtures. Particular mention is made of the organosilanes of Meyer-Simon U.S. Pat. No. 3,842,111. The entire disclosure of Meyer-Simon is hereby incorporated by reference and relied upon.

There are also known reinforcing additives for the mentioned rubber vulcanizates which are produced from the liquid organosilanes of Meyer-Simon U.S. Pat. No. 3,842,111 and silicate fillers (see German Pat. No. 2,255,577 and related Thurn U.S. Pat. No. 3,997,356. The entire disclosure of the Thurn U.S. patent is hereby incorporated by reference and relied upon).

All organosilanes which have previously found entrance in the art for the above mentioned uses are hydrolyzable liquids which upon contact with gaseous or liquid water condense to high molecular weight polysiloxanes with splitting out of alcohol and thereby can at least partially lose their effectiveness as reinforcing additives.

In the rubber working industry all chemical assistants which are liquid at room temperature, thus even the liquid organosilane, have severe disadvantages in comparison to solid chemical assistants, thus the increased difficulty of storing in silos, the increased difficulty in weighing and, above all in the production of mixtures on roller mixer mills, poor mixability.

The conversion of the liquid organosilane into powdery products, for example by mixing with precipitated silica, to be sure carries a certain advantage, but produces no optimum solution because even powdery products are relatively difficult to bring into rubber mixtures, long mixing times are required, dusting occurs and a disturbance and contamination of the environment and the machinery takes place. Furthermore, it has been estabilshed that the deposition of the organosilane occurring on the silicate containing filler particles does not eliminate the sensitivity to hydrolysis of the silane and that there occurs a definite loss in effectiveness in storage of the product. This is expressed for example in a lowering of the final value of cross-linking in rubber vulcanization.

SUMMARY OF THE INVENTION

Surprisingly, it has now been found that in adding the silane preparations of the invention, for example in rubber mixtures, all the above mentioned disadvantages are eliminated and furthermore, unexpected advantages occur.

The new organosilane preparations consist of or consist essentially of:

(a) 30 to 60 weight percent of one or more organosilanes of the formula

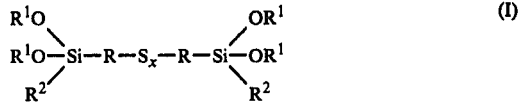

where
$R^1$ is an alkyl group with 1 to 3 carbon atoms,
$R^2$ is an alkyl or alkoxy group with 1 to 3 carbon atoms,
R is an alkylene group with 1 to 5 carbon atoms, and
x has a value from 2.0 to 6.0, and (b) 70 to 40 weight percent of one or more carbon blacks. The sum of (a) and (b) amount to 100 weight percent.

The preferred organosilanes are those of formula (I) wherein $R^2$ is an alkoxy group. These are thus organosilanes which in each case have three alkoxy groups attached to the silicon atoms, which furthermore have an alkylene group (R) with two to four carbon atoms and two to four sulfur atoms (x). Particularly well suited for the purpose of the present invention is the commercial product bis-(3-triethoxysilylpropyl)-tetrasulfide. There can also be added a mixture of several organosilanes for production of the preparation. In this connection "several" means especially 2, 3 or 4.

Examples of organosilanes which can be used in the invention include
3,3'-bis(trimethoxysilylpropyl) disulfide,
3,3'-bis(triethoxysilylpropyl) tetrasulfide,
3,3'-bis(trimethoxysilylpropyl) tetrasulfide,
2,2'-bis(triethoxysilylethyl) tetrasulfide,
3,3'-bis(trimethoxysilylpropyl) trisulfide,
3,3'-bis(triethoxysilylpropyl) trisulfide,
3,3'-bis(trimethoxysilylpropyl) hexasulfide,
2,2'-bis(methoxy diethoxy silyl ethyl) tetrasulfide,
2,2'-bis(tripropoxysilylethyl) pentasulfide,
bis(trimethoxysilylmethyl) tetrasulfide,
2,2'-bis(methyl dimethoxysilylethyl) trisulfide,
2,2'-bis(methyl ethoxypropoxysilylethyl) tetrasulfide,
5,5'-bis(dimethoxymethylsilylpentyl) trisulfide,
3,3'-bis(trimethoxysilyl-2-methoxypropyl) tetrasulfide,
5,5'-bis(triethoxysilylpentyl) tetrasulfide,
4,4'-bis(triethoxysilylbutyl) tetrasulfide,
3,3'-bis(diethoxymethylsilylpropyl) trisulfide,
bis(triethoxysilylmethyl) tetrasulfide.

Particularly advantageous organosilane preparations according to the invention consist of 45 to 57 weight percent of an organosilane of the formula

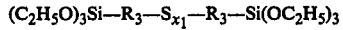

in which $R_3$ is an alkylene group having one to four carbon atoms and $x_1$ has a value of 2.0 to 4.0 and 55 to 43 weight percent of a HAF carbon black with the following test data:

| | |
|---|---|
| BET surface area | 78 m$^2$/g (±3) |
| Average primary particle size (arithmetic average) | 27 nm (±2) |
| pH value | 9 (±1) |
| Dibutyl phthalate absorption | 100 ml/100 g (±5) |

The process of the invention for the production of the new granulate form organosilane preparations is characterized by adding an organosilane or a mixture of organosilanes of the formula

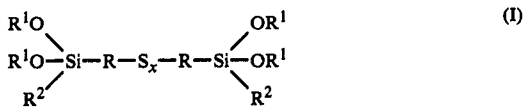

where
- $R^1$ is an alkyl group with 1 to 3 carbon atoms,
- $R^2$ is an alkyl or alkoxy group with 1 to 3 carbon atoms,
- R is an alkylene group with 1 to 5 carbon atoms and
- x has a value from 2.0 to 6.0 to the carbon black and thoroughly mixing using customary, quick acting mixing apparatus such as powder mixers, propeller mixers or bead machines until the granulate formed from 30 to 60 weight percent silane and 70 to 40 weight percent carbon black is dust free. The granules or pellets formed usually have a mean diameter of between 0.3 and 6.0 mm, advantageously between 0.5 and 3.0 mm.

For the production of the organosilane preparations there can be added the known types of carbon black. Preferably there is added the so-called furnace blacks and from this class of blacks preferably the HAF class of blacks. The designation "HAF" is a known abbreviation in the rubber technology for "High Abrasion Furnace". Particularly well suited blacks are the powdery Printex ® types of black of DEGUSSA obtainable in the trade and having BET surface areas between about 30 and 140 $m^2/g$ and average primary particle sizes (arithmetic average) between about 20 and 60 nm (nanometer). Also there can be added mixtures of various types of carbon black for production of the silane preparations of the invention, for example, mixtures of Printex ® 60 and Printex ® 300 or mixtures of Printex ® 30 and Printex ® 300.

For production of the new preparations the starting materials are brought together in suitable apparatus and mixed. The production is generally finished in a few seconds. By maintaining the stated weight proportions there are formed neither powders nor pastes but a grainy or bead form granulate. Apparatus which can be advantageously employed for the production are the known trough shaped powder mixers with rotating propellers. Such mixers have previously been employed for mixing powdery synthetic resins and for the production of PVC (polyvinyl chloride) dry-blends. The granulated preparation is completed with the customary number of revolutions between about 300 and 3000 rpm in a few seconds; for example, within about 10 to 30 seconds.

The new organosilane preparations exhibit many and surprising advantages. They are well suited for storage in silos, they are easy to dosage and mix in particularly well and in shortened mixing times in the rubber mixtures. The effective organosilane is insusceptible to hydrolysis in the preparation; the preparation itself is extraordinarily storage stable. The good dispersability of the preparations in the rubber mixtures is striking. In the conventional vulcanization of rubber mixtures by means of elementary sulfur the organosilane preparations of the invention are more effective than the known silica-silane mixtures of corresponding composition and surprisingly the organosilane preparations are also more effective than is the addition of a corresponding amount of pure organosilane. If the so-called elementary sulfur free cross-linking is carried out according to German OS No. 2,536,674 and related Wolff U.S. application Ser. No. 609,815 filed Sept. 2, 1975 (and continuation Wolff U.S. application 835,848 filed Sept. 22, 1977) the organosilane preparation of the invention is of optimum effectiveness. The entire disclosure of the two Wolff U.S. applications is hereby incorporated by reference and relied upon.

The granulate organosilane preparations of the invention can be used with various types of rubbers. These include, for example, natural rubber, polybutadiene, polyisoprene, e.g., cis-polyisoprene, butadiene-styrene copolymer, butadiene-acrylonitrile copolymer, butyl rubber, as well as other known diene rubbers as for example terpolymers of ethylene, propylene and for example non-conjugated dienes and also non-conjugated polyenes, e.g., ethylene-propylene-cyclooctadiene, ethylene-propylene-norbornadiene, ethylene-propylene dicyclo-pentadiene and ethylene-propylene-cyclododecatriene. Also there can be used trans-polypentenamer, carboxy or epoxy rubbers and the like known elastomers as well as ethylene-vinyl acetate copolymer, ethylene-propylene copolymer as well as mixtures of the named types of rubbers. In a given case chemical derivatives of natural rubber, as well as modified natural rubber can be used. They can also be used with halogen containing rubbers, e.g., polymerized 2-chlorobutadiene and halogenated butyl rubber, e.g., chlorinated butyl rubber and brominated butyl rubber.

In the elementary sulfur free vulcanization there can be used all rubbers still containing double bonds cross-linkable to elastomers, especially halogen free rubbers, preferably the so-called diene elastomers.

With the new organosilane preparations there is thus solved by the invention the problem of producing a silane preparation which based on its composition has a good storage stability, meaning that independent of climatic conditions even after a long storage time its effectiveness as a reinforcing additive in rubber mixtures is completely guaranteed. It has proven surprisingly that the addition of carbon black as the carrier component for the organosilane preparation results in a decisive industrial advance.

Unless otherwise indicated all parts and percentages are by weight.

The organosilane-carbon black granulates consist essentially of or consist of these materials.

DESCRIPTION OF THE PREFERRED EMBODIMENTS

EXAMPLE 1

As the carbon black there was employed Printex ® 30, a carbon black having the following test data:

| | |
|---|---|
| BET surface area | 78 $m^2/g$ |
| Average primary particle size (arithmetic average) | 27 nm |
| pH value | 9 |
| Dibutyl phthalate absorption (abbreviated DBP-Abs.) (ASTM D 2414) | 100 ml/100 g |

There were weighed into a trough shaped powder mixer equipped with propeller like mixing implements and having a capacity of 150 liters 10 kg of furnace black Printex ® 30, then 10 kg of bis-(3-triethoxysilyl-propyl)-tetrasulfide (known as Si 69) were added and both components worked and homogenized for 25 seconds at 360 rpm. The apparatus employed is described in German OS No. 1,592,861. After raising the discharge lid there were discharged 20 kg of a granulate having a particle size of about 0.8 mm. The granulate was dust free, non-adhering and had good pourability.

EXAMPLE 2

The following organosilane preparations were prepared in a continuous procedure rather than in a discontinuous process. For this purpose there was used the bead forming machine described in FIG. 2 of German Pat. No. 2,147,503 and FIG. 2 of related Rothbuhr U.S. Pat. No. 3,852,399. The entire disclosure of the Rothbuhr U.S. patent is hereby incorporated by reference and relied upon. Accordingly, there were produced from 80 kg of Printex ® 30 per hour and 80 kg of silane Si 69 per hour 160 kg per hour of practically dust free granulate in bead form.

EXAMPLE 3

The following types and amounts of carbon black as well as the silane Si 69 in the stated amounts were employed for the production of silane preparations of the invention.

| Type and Amount of Carbon Black in Weight Percent | BET-Surface Area in m²/g | DBP-Abs. According to ASTM D 2414 in ml/100 g | Silane Si 69 in Weight Percent |
|---|---|---|---|
| Printex ® 200 : 70 | 45 | 44 | 30 |
| Printex ® 400 : 65 | 100 | 48 | 35 |
| Printex ® 3 : 45 | 80 | 135 | 55 |
| Printex ® 3 H : 40 | 78 | 155 | 60 |

The production was carried out in the manner described in Example 1. The silane preparations produced exhibited optimum granulate properties: bead form of 0.8 to 1.0 mm average particle size and a bead abrasion of 0.5 to 2.0% (see DIN 53 583). (DIN is an abbreviation for German Industrial Standard.)

EXAMPLE 4

Using the procedure described in Example 1 there were homogenized with each other in each case in a 7-liter trough mixer:

(a) 200 g Printex ® 30 with 200 g of the silane (CH₃O)₃Si(CH₂)₃—S—S—(CH₂)₃Si(OCH₃)₃

(b) 200 g Printex ® 30 with 200 g of the silane (CH₃O)₃Si(CH₂)₃—S—S—S—(CH₂)₃Si(OCH₃)₃

(c) 200 g Printex ® 30 with 200 g of the silane (CH₃O)₃Si(CH₂)₃—S—S—S—S—(CH₂)₃Si(OCH₃)₃

The mixing time was 10 seconds at 1,400 rpm. In this case also there were obtained dust free, flowable, readily workable granulates.

EXAMPLE 5

To investigate the storage stability and determine the effectiveness depending on the duration of storage on the one hand a known, powdery mixture of 50 weight percent silica Ultrasil ® VN₃ (finely divided highly active precipitated silica) and 50 weight percent bis-(triethoxysilylpropyl)-tetrasulfide and on the other hand a granulated, dust free preparation of 50 weight percent carbon black Printex ® 30 and 50 weight percent of bis-(triethoxysilylpropyl)-tetrasulfide were incorporated in each case into a synthetic rubber mixture based on a styrene-butadiene rubber (SBR 1500). The rubber mixtures had the following composition:

| | |
|---|---|
| Styrene-butadiene rubber (SBR 1500) | 100 parts by weight |
| Silica filler (Ultrasil ® VN₃) | 35 parts by weight |
| Organosilane preparation or mixture (see above) | 10 parts by weight |
| Zinc oxide | 3 parts by weight |
| Stearic acid | 2 parts by weight |
| Sulfur | 2 parts by weight |
| Cyclohexylbenzothiazole sulfenamide accelerator | 1 part by weight |

These mixtures were investigated at 155° C. in a Monsanto-Rheometer at an amplitude of 3° and 3 cycles.

$D\infty$ = maximum torque $Da$ = minimum torque $D\infty - Da$ = torque caused by cross-linking (cross-linking final value)

$t_I$ = incubation time $K_V^J$ = velocity constant of the cross-linking reaction according to first order time law $T_{5\%}$ = time for the cross-linking reaction of 5% of the total amount of cross-linking $t_{95\%}$ = time for the cross-linking reaction of 95% of the total amount of cross-linking

Test Results (a) Using the granulated, dust free preparation of 50 weight % carbon black Printex ® 30 and 50 weight % bis-(triethoxysilylpropyl)-tetrasulfide

| | | Results with Mixing of the Preparation Immediately After Production | Results with Mixing After Storage of the Preparation for One Year |
|---|---|---|---|
| $D\infty$ | mkp | 1.186 | 1.193 |
| $Da$ | mkp | 0.071 | 0.078 |
| $D\infty - Da$ | mkp | 1.115 | 1.115 |
| $t_I$ | sec | 699 | 679 |
| $K_V^J \times 10^3$ | min⁻¹ | 131 | 140 |
| $t_{5\%}$ | min | 10.4 | 10.2 |
| $t_{95\%}$ | min | 33.3 | 32.6 |

(b) Using the powdery mixture of 50 weight percent silica filler and 50 weight percent bis-(troethoxysilylpropyl)-tetrasulfide for comparison

| | | Results with Mixing of the Preparation Immediately After Production | Results with Mixing After Storage of the Preparation for One Year |
|---|---|---|---|
| $D\infty$ | mkp | 1.190 | 1.141 |
| $Da$ | mkp | 0.089 | 0.141 |
| $D\infty - Da$ | mkp | 1.101 | 1.000 |
| $t_I$ | sec | 685 | 698 |
| $K_V^J \times 10^3$ | min⁻¹ | 117 | 69 |
| $t_{5\%}$ | min | 10.0 | 10.5 |
| $t_{95\%}$ | min | 30.0 | 55.0 |

After one year storage time the granulated, dust free preparation of 50 weight percent carbon black Printex ® 30 and 50 weight percent bis-(triethoxysilylpropyl)-tetrasulfide showed no recognizable change in test mixture properties. The powdery mixture of silica filler and silane on the contrary showed a clear reduction in cross-linking final value ($D\infty - Da$) and a characteristic reduction of the velocity constant of the cross-linking reaction $K_V^J$, which meant an increase in the vulcanization time to practically double ($t_{95\%}$).

The new granulate formed organosilane preparations because of their very good storage stability, resistance to hydrolysis and their surprisingly good workability have their predominant use in rubber mixtures and compositions of all types, both in so-called master batches and also directly in the mixtures ready for use. The concept "all types" refers particularly to the known types of rubber both of natural and synthetic source and to the customary fillers employed in rubber technology such as preferably carbon black but also including the known white fillers, such as silica fillers, silicate fillers, kaolins, clay, carbonate (e.g., calcium carbonate and barium carbonate), quartz and kieselguhr as well as mixtures of the mentioned fillers including and preferably carbon black.

What is claimed is:

1. A granulate organosilane composition consisting of (a) 30 to 60 weight percent of an organosilane of the formula

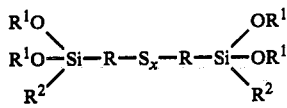

where $R^1$ is an alkyl group with 1 to 3 carbon atoms, $R^2$ is an alkyl or alkoxy group with 1 to 3 carbon atoms, R is an alkylene group with 1 to 5 carbon atoms and x has a value from 2.0 to 6.0, and (b) 70 to 40 weight percent of carbon black.

2. A granulate organosilane composition according to claim 1 wherein the carbon black is a furnace black.

3. A granulate composition according to claim 2 wherein the carbon black is an HAF black.

4. A granulate composition according to claim 3 wherein the granulates have an average particle size of about 0.8 to 1.0 mm.

5. A granulate composition according to claim 4 wherein the organosilane is bis-(3-triethoxysilylpropyl)-tetrasulfide.

6. A granulate composition according to claim 5 consisting of 45 to 57 weight % of the organosilane and 55 to 43 weight % of the carbon black.

7. A granulate organosilane composition according to claim 1 wherein the granulates have an average particle size of about 0.8 to 1.0 mm.

8. A granulate organosilane composition according to claim 1 consisting of 45 to 57 weight percent of an organosilane of the formula $(C_2H_5O)_3Si-R_3-S_{x_1}-R_3-Si(OC_2H_5)_3$ where $R_3$ is an alkylene group with 1 to 4 carbon atoms and $x_1$ is a number between 2.0 and 4.0, and 55 to 43 weight percent of an HAF black having the following properties

| BET surface area | 78 m²/g (±3) |
| --- | --- |
| Average primary particle size (arithmetic average) | 27 nm (±2) |
| pH | 9 (±1) |
| Dibutyl phthalate absorption | 100 ml/100 g (±5) |

9. A granulate organosilane composition according to claim 1 consisting of 30 weight percent of an organosilane of the formula $(C_2H_5O)_3Si-R_3-S_{x_1}-R_3-Si(OC_2H_5)_3$ where $R_3$ is an alkylene group with 1 to 4 carbon atoms and $x_1$ is a number between 2.0 and 4.0, and 70 weight percent of a furnace black having the following properties

| BET surface area | 45 m²/g (±3) |
| --- | --- |
| Average primary particle size (arithmetic average) | 56 nm (±4) |
| pH | 9 (±1) |
| Dibutyl phthalate absorption | 44 ml/100 g (±5) |

10. A granulate organosilane composition according to claim 1 consisting of 60 weight percent of an organosilane of the formula $(C_2H_5O)_3Si-R_3-S_{x_1}-R_3-Si(OC_2H_5)_3$ where $R_3$ is an alkylene group with 1 to 4 carbon atoms and $x_1$ is a number from 2.0 and 4.0, and 40 weight percent of a carbon black having the following properties

| BET surface area | 78 m²/g (±3) |
| --- | --- |
| Average primary particle size | 27 nm (±2) |
| pH | 9 (±1) |
| Dibutyl phthalate absorption | 155 ml/100 g (±5) |

11. A process for the production of the granulate organosilane composition of claim 1 consisting of mixing the organosilane (a) with the carbon black (b) until there are formed dust free granulates.

* * * * *